United States Patent [19]
Baldwin et al.

[11] Patent Number: 5,271,737
[45] Date of Patent: Dec. 21, 1993

[54] TIBIAL PROSTHETIC IMPLANT WITH OFFSET STEM

[75] Inventors: James L. Baldwin, Portland, Oreg.; Steven I. Whitlock, Austin, Tex.

[73] Assignee: U.S. Medical Products, Inc., Austin, Tex.

[21] Appl. No.: 940,441

[22] Filed: Sep. 4, 1992

[51] Int. Cl.⁵ .............................................. A61F 2/38
[52] U.S. Cl. ...................................................... 623/20
[58] Field of Search ........................... 623/18, 20, 16

[56] References Cited

U.S. PATENT DOCUMENTS

| Re. 29,757 | 9/1978 | Helfet | 623/20 |
|---|---|---|---|
| 4,205,400 | 6/1980 | Shen et al. | 623/20 |
| 4,255,439 | 8/1980 | Gold et al. | 623/20 |
| 5,137,536 | 8/1992 | Koshino | 623/20 |

FOREIGN PATENT DOCUMENTS 0189253  7/1986  European Pat. Off. .............. 623/20

Primary Examiner—David Isabella
Attorney, Agent, or Firm—Shaffer & Culbertson

[57] ABSTRACT

A tibial prosthetic implant includes a base or base plate with an offset tibial stem. The base includes an inferior surface adapted to abut a resected surface of a patient's tibia and forms a base for articulating surfaces adapted to articulate with the patient's femoral condyles. The longitudinal center axis of the tibial stem extends from the inferior surface of the base and is offset from a center of the base. The offset places the stem in position to extend into the central canal of the tibia so that it does not substantially interfere with the cortical bone when the inferior surface of the base substantially abuts and aligns with the resected surface of the tibia.

12 Claims, 3 Drawing Sheets

TIBIAL PROSTHETIC IMPLANT WITH OFFSET STEM

BACKGROUND OF THE INVENTION

This invention relates to implants for total knee arthroplasty, and more particularly, to an improved stemmed tibial prosthetic implant.

Total knee arthroplasty involves providing new articulating surfaces for the tibia, femur, and patella. The most common technique for providing new articulating surfaces for the tibia involves resecting an upper portion of the tibia and then attaching a prosthetic implant to the tibia over the resected surface. The tibial implant includes a base adapted to abut the resected surface of the tibia and an articulating portion which includes the new articulating surfaces. The base of the implant has a shape that is adapted to generally approximate the shape of the resected surface of the tibia so that the implant generally aligns with the resected surface when the base is properly attached to the tibia.

The implant may also include a plurality of pegs extending from the lower or inferior surface of the base. The pegs are adapted to extend into the bone of the tibia when the implant is secured to the resected surface and provide enhanced torsional stability about the longitudinal axis of the tibia. In addition or alternatively to pegs, a stem may extend from the inferior surface of the base so as to extend a substantial distance into the tibia when the implant is attached over the resected surface. Tibial stems provide further torsional stability and axial strength by providing more surface area for contact with the bone. The stem also provides a "keel" effect to prevent the tibial implant from toggling or wobbling.

The tibia itself comprises an outer layer of hard cortical bone and a central canal of relatively soft cancellous bone. Much of the strength of the tibia is provided by the cortical bone. In a normally shaped tibia, the central canal is offset from the center of the tibial articulating surfaces or the center of the tibial plateau. The stems of prior tibial implants were, however, positioned centrally to the implant base. Although the central location of the stem allowed a particular implant to be used for either the right or left knee, this stem position resulted in serious drawbacks. The primary drawback was that the centrally located stem was substantially offset from the center of the tibial canal itself when the base of the implant was aligned with the resected tibial surface. In fact, stems located centrally to the base occasionally contacted the posterior cortical bone of the tibia. This interference with the cortical bone sometimes prevented the base of the implant from seating flush against the resected surface of the tibia, thereby inhibiting adequate initial stability and fixation which is essential for successful knee arthroplasty.

SUMMARY OF THE INVENTION

It is a broad object of the invention to provide a stemmed tibial implant that overcomes the above-described problems and others associated with prior tibial implants.

In order to accomplish this object, a tibial implant according to the invention includes a stem that is offset from the center of the implant base. Similarly to prior tibial implants, the present implant includes a base, an articulating portion, and attachment means for securing the implant to a patient's tibia during the implantation procedure. However, the tibial implant according to the invention also includes a stem extending from a point on the inferior surface of the base that is offset from a center point of the base. This offset enables the stem to extend into the central tibial canal when the implant is attached to the tibia with the inferior surface of the base abutting and aligning with the resected surface. The offset stem does not extend into or otherwise interfere with the cortical bone of the tibia. Also, optimal keel effect is achieved when the stem is central to the condylar weight bearing surface, providing equally dense bone on either side of the stem.

The optimum stem offset varies from patient to patient. Normally, however, the stem is offset anteriorly or forward of the center point of the base and also medially or to the inside with respect to the center point of the base. The anterior offset is preferably in the range of approximately 59% to 68% of the total anterior-posterior medial condyle depth dimension as measured from the outermost posterior edge of the base. The medial offset is preferably in the range of approximately 52% to 55% of the total base medial-lateral width dimension, as measured from the outermost lateral edge of the base.

The stem may be cylindrical in shape, square, or any other shape desired for the particular application. The preferred stem, however, has a cruciate transverse cross-sectional shape and comprises a central root portion with four webs extending at different angular orientations from the root portion. Each web extends generally toward a different corner of the base and includes an enlarged portion proximal to the base and a relatively narrow portion at the end of the stem distal to the base.

These and other objects, advantages, and features of the invention will be apparent from the following description of the preferred embodiments, considered along with the accompanying drawings.

DESCRIPTION OF THE PREFERRED EMBODIMENTS

Figure 1:
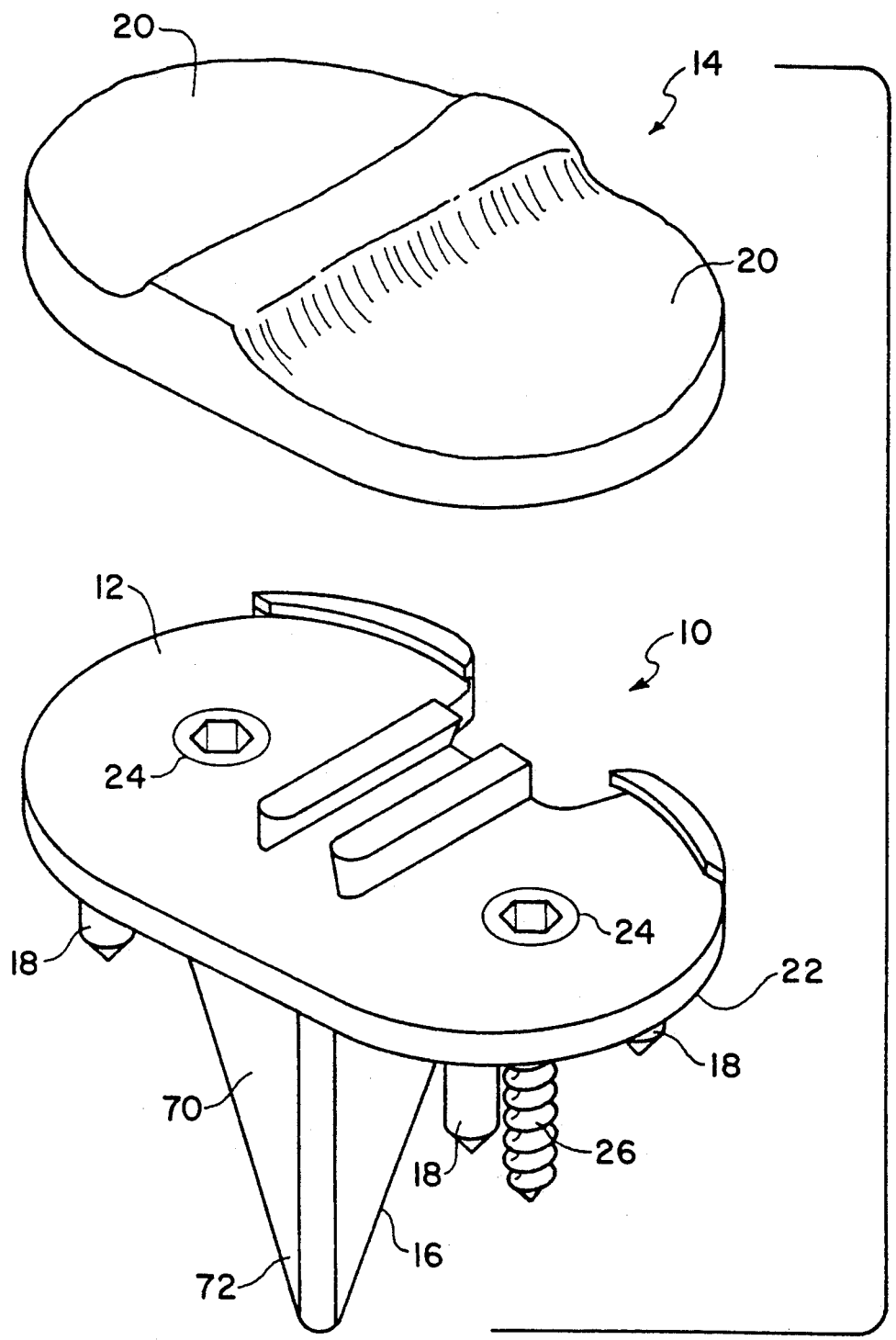
FIG. 1 is an exploded view in perspective of a stemmed tibial prosthetic implant embodying the principles of the invention.
Figure 2:
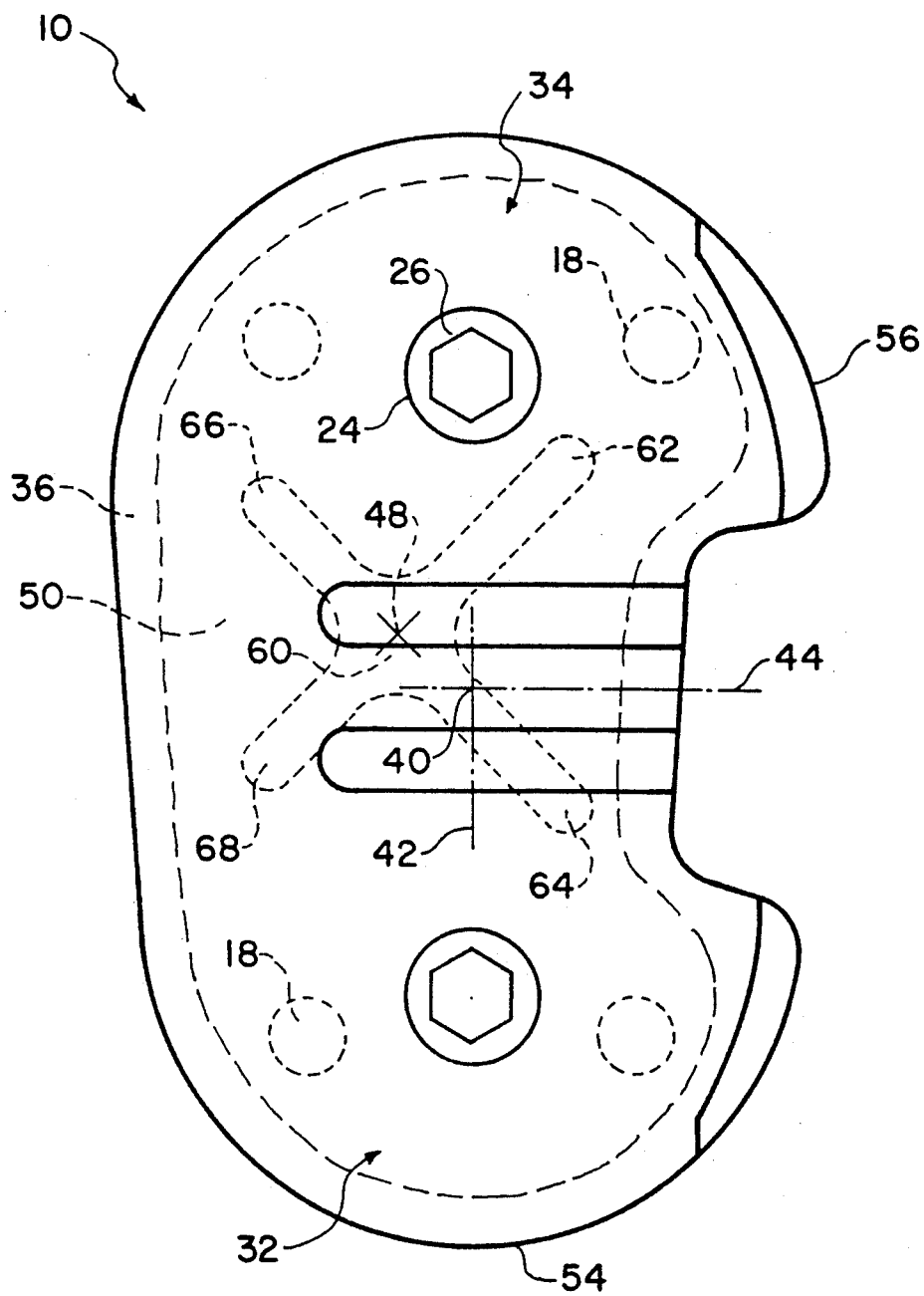
FIG. 2 is a top plan view of the prosthetic implant shown in FIG. 1 as attached to a patient's tibia.
Figure 3:
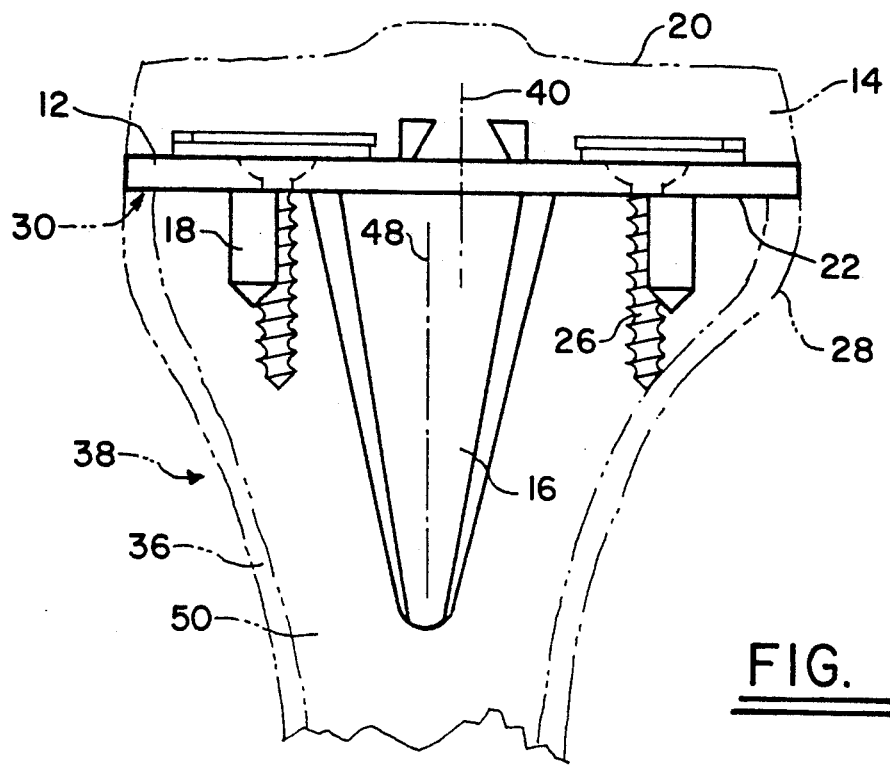
FIG. 3 is a front view of the attached prosthetic implant shown in FIG. 2 with the tibia shown in phantom.

Referring particularly to FIG. 1 a tibial implant 10 embodying the principles of the invention includes a base 12 and an articulating portion 14. A stem 16, and preferably, a plurality of pegs 18 are connected to the base 12 of the implant. As shown in FIGS. 2 and 3, the base 12 also includes two openings 24 for receiving bone screws 26. The bone screws 26 along with the openings 24 form attachment means for attaching the implant 10 to the patient's tibia as described below.

Although the base 12 and articulating portion 14 may be integrally formed, the preferred form of the invention shown in the figures is modular with a base plate forming the base 12 and a separate insert comprising the articulating portion 14. The base plate and insert are adapted to connect together by suitable means to form the implant 10. The articulating portion or insert 14 is preferably formed from a suitable plastic material and includes articulating surfaces 20 adapted to articulate with the femoral condyles (not shown) of the patient's knee. The preferred base or base plate 12 comprises a planar plate of a biologically compatible material and includes a lower or inferior surface 22 to which the stem 16 and pegs 18 are connected. The stem 16 and pegs 18 may be integrally formed with the base 12 or may be formed separately and connected by suitable means.

Figure 4:
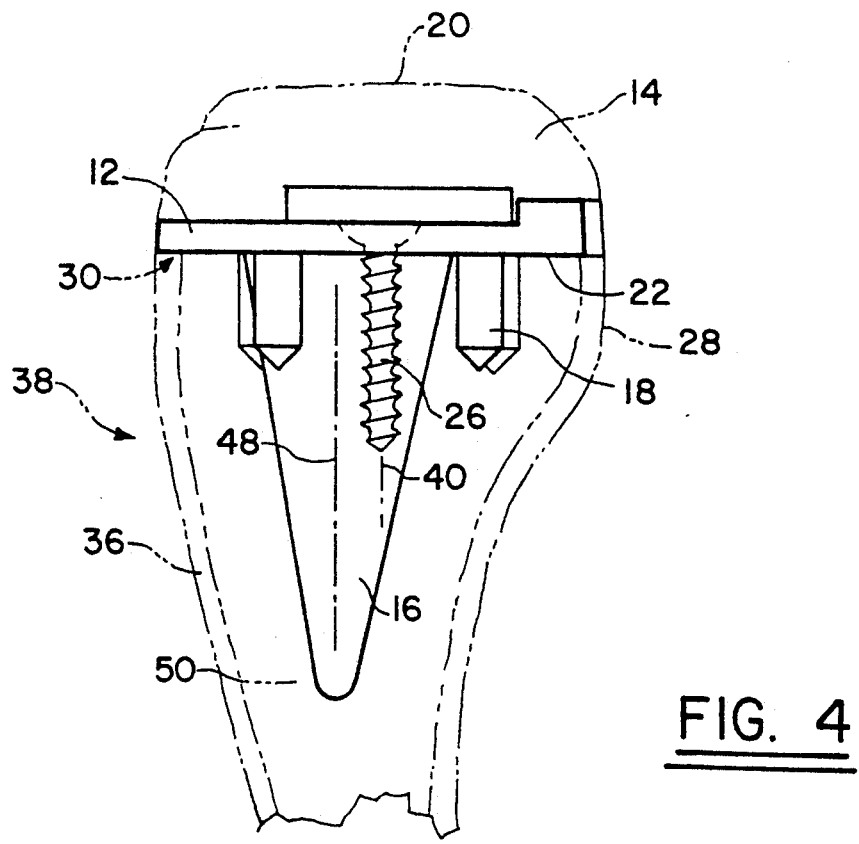
FIG. 4 is a right side view of the attached implant shown in FIG. 2 with the tibia shown in phantom.

Referring to FIGS. 2 through 4, the transverse cross-sectional shape of the base 12 and the shape of the inferior surface 22 are both adapted to approximate the shape of the tibial plateau 28, and particularly, a resected surface 30 through the tibial plateau. As used herein a transverse cross-section through the base 12 is along a plane extending parallel to the plane of the inferior surface 22. Also, in order to better approximate the shape of the resected surface 30, the base 12 is asymmetrical about a medial-lateral center line. That is, base 12 includes a lateral portion 32 adapted to approximate the shape of the lateral tibial plateau and a larger medial portion 34 adapted to approximate the shape of the medial tibial plateau. This asymmetrical base shape serves to maximize the base contact or overlap with the cortical bone 36 of the tibia 38 thereby providing strength while minimizing any overhang over the cortical bone which could interfere with soft tissue extending to or through the knee joint (not shown). Regardless of the shape of the base 12, the base has a center 40 that is defined by the intersection of the medial-lateral center line 42 and the anterior-posterior center line 44 as shown in FIG. 2.

Referring still to FIGS. 2 through 4, the longitudinal axis 48 of the stem 16 is offset from the center 40 of the base 12. The offset enables the stem 16 to extend into the central canal 50 of the tibia 38 when the base 12 is positioned over the resected surface 30 with the inferior surface 22 abutting and generally aligned with the resected surface. As shown particularly in FIGS. 3 and 4, the stem 16 does not extend into the cortical bone 36 of the tibia 38. Thus, the cortical bone 36 below the resected surface 30 is left intact with its full natural strength. Also, since the stem 16 does not extend into the cortical bone 36, the implantation procedure does not require boring or broaching the hard cortical bone and the trauma to the area that such boring or broaching necessitates. Furthermore, optimal keel effect is achieved when the stem is central to the condylar weight bearing surface, providing equally dense bone on either side of the stem.

As shown best in FIG. 2, the offset required for the desired stem position is both medial and anterior from the center 40 of the base 12 for normally shaped tibias. Although the exact offset will vary from patient to patient, the preferred offset in the medial direction is between 52% to 55% of the total medial-lateral width dimension as measured from the outermost lateral edge 54 of the base 12 along the anterior-posterior center line 42. The preferred offset in the anterior direction is in a range between 59% to 68% of the total anterior/posterior medial condyle depth dimension as measured from the outermost posterior edge 56 of the base 12 along the medial-lateral center line 44.

Although any stem shape may be employed in a tibial implant embodying the principles of the invention, the preferred stem 16 forms a cruciate shape. The cruciate-shaped stem 16 includes a center root portion 60 and a plurality of longitudinally aligned webs extending from the root at different angular orientations about the stem longitudinal axis 48. In particular, the stem 16 includes a medial-posterior web 62, a lateral-posterior web 64, a medial-anterior web 66, and a lateral-anterior web 68. Each web includes an enlarged portion 70 at the end proximal to the base 12, narrowing down continuously to a relative narrower portion 72 at the end of the stem distal to the base. Also, as shown best in FIG. 2, the enlarged portions 70 of the lateral-posterior and medial-posterior webs 64 and 62 extend further from the center root 60 of the stem 16 than the enlarged portions of the lateral-anterior and medial-anterior webs 68 and 66. These web shapes generally follow the internal contour of the central canal 50 of the tibia to maximize contact with the cancellous bone in the canal.

Implanting the stemmed tibial implant 10 embodying the principles of the invention includes first resecting an upper portion of the patient's tibia 38 to remove the natural articulating surfaces and form a suitable resected surface 30. The resected surface 30 is preferably planar and extends substantially transversely to the longitudinal axis of the tibia 38 in the anterior-posterior view and parallel to the anatomic posterior slope of the tibia in the medial-lateral view of the tibia.

Once the desired resected surface 30 is produced, the base 12 of the implant 10 shown in FIGS. 1 through 4 is positioned with the inferior surface 22 abutting and generally aligned with the resected surface. The base 12 is fixed in place with bone screws 26 extending through the screw openings 24 in the base. With the inferior surface 22 of the base 12 abutting the resected surface 30 of the patient's tibia 38 and with the base properly aligned, the stem 16 extends into the central canal 50 of the tibia and does not interfere with the cortical bone 36. Although some broaching will be required to produce an opening for the stem 16, the offset position of the stem will necessitate little, if any, broaching of the cortical bone 36, only broaching of the much softer cancellous bone in the central tibial canal 50.

The above described preferred embodiments are intended to illustrate the principles of the invention, but not to limit the scope of the invention. Various other embodiments and modifications to these preferred embodiments may be made by those skilled in the art without departing from the scope of the following claims. For example, although the embodiment shown in the drawings includes a plurality of pegs 18, an implant embodying the principles of the invention may include only the offset stem 16. Also, although not shown specifically in the drawings, the inferior surface 22 of the base 12, the pegs 18 if present, and the stem 16 may all include a layer of porous material adapted to provide enhanced bonding to the bone.

We claim:

1. A tibial prosthetic implant comprising:
   (a) a base having an inferior surface adapted to substantially abut a resected surface of a patient's tibia and a transverse cross-sectional shape adapted to approximate a peripheral shape of the resected surface of the tibia;
   (b) an articulating portion connected to the base, the articulating portion of the implant having articulating surfaces opposite the inferior surface of the base for articulating with a patient's femoral condyles;
   (c) attachment means for securing the base to the resected surface of the tibia so that the inferior surface of the base substantially abuts and aligns with the resected surface of the tibia; and (d) a tibial stem extending from the inferior surface of the base, the tibial stem having a longitudinal center axis that is offset anteriorly and medially from a center of the base such that the stem is in position to extend into the central canal of the patient's tibia without substantially interfering with the cortical bone of the tibia when the inferior surface of the base abuts and aligns with the resected surface of the tibia.

2. The tibial prosthetic implant of claim 1 wherein the tibial stem includes:
(a) a central root portion extending an entire length of the tibial stem; and
(b) a medial-posterior web extending generally medially and posteriorly from the stem central root portion, a lateral-posterior web extending generally laterally and posteriorly from the stem central root portion, a medial-anterior web extending substantially medially and anteriorly from the stem central root portion, and a lateral-anterior web extending generally laterally and anteriorly from the stem central root portion, each web having an enlarged portion at an end of the stem proximal to the inferior surface of the base and a relatively narrower portion at an end of the stem distal of the base.

3. A tibial prosthetic implant comprising:
(a) a base having an inferior surface adapted to substantially abut a resected surface of a patient's tibia and a transverse cross-sectional shape adapted to approximate a peripheral shape of the resected surface of the tibia;
(b) an articulating portion connected to the base, the articulating portion of the implant having articulating surfaces opposite the inferior surface of the base for articulating with a patient's femoral condyles;
(c) attachment means for securing the base to the resected surface of the tibia so that the inferior surface of the base substantially abuts and aligns with the resected surface of the tibia; and
(d) a tibial stem extending from the inferior surface of the base, the tibial stem having a longitudinal center axis that is offset medially from a center of the base such that the stem is in position to extend into the central canal of the patient's tibia without substantially interfering with the cortical bone of the tibia when the inferior surface of the base abuts and aligns with the resected surface of the tibia.

4. The tibial prosthetic implant of claim 3 wherein:
(a) the longitudinal center axis of the tibial stem is offset medially from the center of the base a distance that is between 52% and 55% of a total medial-lateral width dimension of the base as measured from an outermost lateral edge of the base.

5. A base plate for a modular tibial prosthetic implant, the base plate comprising:
(a) a plate of material having an inferior surface adapted to substantially abut a resected surface of a patient's tibia; and
(b) a tibial stem extending from the inferior surface of the plate, the tibial stem having a longitudinal center axis that is offset anteriorly and medially from a center of the plate such that the stem is in position to extend into the central canal of the patient's tibia without substantially interfering with the cortical bone of the tibia when the inferior surface of the plate substantially abuts the resected surface of the tibia and the center of the plate aligns with a center of the resected surface of the tibia.

6. The tibial prosthetic implant of claim 5 wherein:
(a) the longitudinal center axis of the tibial stem is offset anteriorly from the center axis of the plate a distance that is between 59% to 68% of a total anterior-posterior medial condyle depth dimension of the plate as measured from an outermost posterior edge of the plate; and
(b) the longitudinal center axis of the tibial stem is offset medially from the center of the plate a distance that is between 52% to 55% of a total medial-lateral width dimension of the plate as measured from an outermost lateral edge of the plate.

7. A base plate for a modular tibial prosthetic implant, the base plate comprising:
(a) a plate of material having an inferior surface adapted to substantially abut a resected surface of a patient's tibia; and
(b) a tibial stem extending from the inferior surface of the plate, the tibial stem having a longitudinal center axis that is offset medially from a center of the plate, such that the stem is in position to extend into the central canal of the patient's tibia without substantially interfering with the cortical bone of the tibia when the inferior surface of the plate substantially abuts the resected surface of the tibia and the center of the plate aligns with a center of the resected surface of the tibia.

8. The base plate of claim 7 wherein:
(a) a longitudinal center axis of the tibial stem is offset medially from the center of the plate a distance that is between 52% to 55% of a total medial-lateral width dimension of the plate as measured from an outermost lateral edge of the plate.

9. A tibial prosthetic implant of the type having a base that includes an inferior surface adapted to substantially abut a resected surface of a patient's tibia so as to support articulating surfaces that are adapted to articulate with the patient's femoral condyles, wherein the improvement comprises:
(a) a tibial stem extending from the inferior surface of the base, the tibial stem having a longitudinal center axis that is offset anteriorly and medially from a center of the base such that the stem is in position to extend into the central canal of the patient's tibia without substantially interfering with the cortical bone of the tibia when the inferior surface of the base abuts the resected surface of the tibia and the center of the base aligns with a center of the resected surface of the tibia.

10. The tibial prosthetic implant of claim 9 wherein:
(a) a longitudinal center axis of the tibial stem is offset anteriorly from the center of the base a distance that is between 59% to 68% of a total anterior-posterior medial condyle depth dimension of the base as measured from an outermost posterior edge of the base; and
(b) the longitudinal center axis of the tibial stem is offset medially from the center of the base a distance that is between 52% to 55% of a total medial-lateral width dimension of the base as measured from any outermost lateral edge of the base.

11. A tibial prosthetic implant of the type having a base that includes an inferior surface adapted to substantially abut a resected surface of a patient's tibia so as to support articulating surfaces that are adapted to articulate with the patient's femoral condyles, wherein the improvement comprises:

(a) a tibial stem extending from the inferior surface of the base, the tibial stem having a longitudinal center axis that is offset medially from a center of the base such that the stem is in position to extend into a central canal of the patient's tibia when the inferior surface of the base abuts the resected surface of the tibia and the center of the base aligns with a center of the resected surface of the tibia.

12. The tibial prosthetic implant of claim 11 wherein:
(a) the longitudinal center axis of the tibial stem is offset medially from the center of the base a distance that is between 52% to 55% of a total medial-lateral width dimension of the base as measured from an outermost lateral edge of the base.

* * * * *